US00PP36971P2

(12) United States Plant Patent
Koot

(10) Patent No.: US PP36,971 P2
(45) Date of Patent: Sep. 16, 2025

(54) ***SANVITALIA* PLANT NAMED 'Dosansusugo24'**

(50) Latin Name: *Sanvitalia procumbens*
Varietal Denomination: Dosansusugo24

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 19/055,251

(22) Filed: Feb. 17, 2025

(51) Int. Cl.
*A01H 6/14* (2018.01)
*A01H 5/02* (2018.01)

(52) U.S. Cl.
USPC ..... Plt./476
CPC ..... *A01H 6/14* (2018.05); *A01H 5/02* (2013.01)

(58) Field of Classification Search
USPC ..... Plt./476
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Sanvitalia* plant named 'Dosansusugo24', characterized by its relatively compact, semi-upright and mounding plant habit; relatively moderately vigorous growth habit; freely branching habit; early and freely flowering habit; inflorescences with bright yellow-colored ray florets and yellowish green-colored disc florets; and good container and garden performance.

1 Drawing Sheet

Botanical designation: *Sanvitalia procumbens.*
Cultivar denomination: 'DOSANSUSUGO24'.

CROSS REFERENCED TO CLOSELY-RELATED APPLICATION:

A European Community Plant Breeder's Rights application for the instant plant was filed by the Applicant/Assignee, Dümmen Group B.V. of De Lier, The Netherlands on Oct. 2, 2023, application number 2023/2064 and published on Dec. 15, 2023. Foreign priority is not claimed to this application.

BACKGROUND OF THE INVENTION

The present invention relates to a new and distinct cultivar of *Sanvitalia* plant, botanically known as *Sanvitalia procumbens,* commonly known as Creeping Zinnia and hereinafter referred to by the name 'Dosansusugo24'.

The new *Sanvitalia* plant is a product of a planned breeding program conducted by the Inventor in Rheinberg, Germany. The objective of the breeding program is to create new compact and mounding *Sanvitalia* plants with numerous attractive inflorescences.

The new *Sanvitalia* plant originated from a cross-pollination conducted by the Inventor in Rheinberg, Germany in July 2020 of a proprietary selection of *Sanvitalia procumbens* identified as code number LL19-K0006, not patented, as the female, or seed, parent with a proprietary selection of *Sanvitalia procumbens* identified as code number LL20-K0004, not patented, as the male, or pollen, parent. The new *Sanvitalia* plant was discovered and selected by the Inventor as a single flowering plant from within the progeny of the stated cross-pollination in a controlled greenhouse environment in Rheinberg, Germany in April 2021.

Asexual reproduction of the new *Sanvitalia* plant by vegetative cuttings in a controlled environment in Rheinberg, Germany since April, 2021 has shown that the unique features of this new *Sanvitalia* plant are stable and reproduced true to type in successive generations.

SUMMARY OF THE INVENTION

Plants of the new *Sanvitalia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dosansusugo24'. These characteristics in combination distinguish 'Dosansusugo24' as a new and distinct *Sanvitalia* plant:

1. Relatively compact, semi-upright and mounding plant habit.
2. Relatively moderately vigorous growth habit.
3. Freely branching habit.
4. Early and freely flowering habit.
5. Inflorescences with bright yellow-colored ray florets and yellowish green-colored disc florets.
6. Good container and garden performance.

Plants of the new *Sanvitalia* differ primarily from plants of the female and male parent selections in plant habit as plants of the new *Sanvitalia* are more compact than and not as vigorous as plants of the female and male parent selections.

Plants of the new *Sanvitalia* can be compared to plants of *Sanvitalia procumbens* 'Disangob21', not patented. In side-by-side comparisons, plants of the new *Sanvitalia* differ from plants of 'Disangob21' in the following characteristics:

1. Plants of the new *Sanvitalia* are more compact than and not as vigorous as plants of 'Disangob21'.

2. Plants of the new *Sanvitalia* are more freely branching than plants of 'Disangob21'.
3. Plants of the new *Sanvitalia* have shorter internodes than plants of 'Disangob21' giving a denser appearance.
4. Plants of the new *Sanvitalia* have smaller leaves than plants of 'Disangob21'.
5. Plants of the new *Sanvitalia* are more freely flowering than plants of 'Disangob21'.
6. Inflorescences of plants of the new *Sanvitalia* have bright yellow-colored ray florets whereas inflorescences of plants of 'Disangob21' have orangish yellow-colored ray florets.

BRIEF DESCRIPTION OF THE PHOTOGRAPH

The accompanying photograph illustrates the overall appearance of the new *Sanvitalia* plant showing the colors as true as it is reasonably possible to obtain in colored reproductions of this type. Colors in the photograph may differ slightly from the color values cited in the detailed botanical description which accurately describe the colors of the new *Sanvitalia* plant.

The photograph comprises a side perspective view of a typical flowering plant of 'Dosansusugo24' grown in a container.

DETAILED BOTANICAL DESCRIPTION

The aforementioned photograph and following observations, measurements and values describe plants grown during the spring and summer in 13-cm containers in a glass-covered greenhouse in Rheinberg, Germany and under cultural practices typical of commercial *Sanvitalia* production. During the production of the plants, day and night temperatures averaged 18° C. and light levels averaged 4,500 lux. Plants were twelve weeks from planting rooted young plants when the photograph was taken and 25 weeks from planting rooted young plants when the description was taken. In the following description, color references are made to The Royal Horticultural Society Colour Chart, Fifth Edition, except where general terms of ordinary dictionary significance are used.

Botanical classification: *Sanvitalia procumbens* 'Dosansusugo24'.

Parentage:

*Female parent*.—Proprietary selection of *Sanvitalia procumbens* identified as code number LL19-K0006, not patented.

*Male parent*.—Proprietary selection of *Sanvitalia procumbens* identified as code number LL20-K0004, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 155B in color, actual color of the roots is dependent on substrate composition, water quality, fertilizers, substrate temperature and age of roots.

*Rooting habit*.—Freely branching; dense.

Plant description:

*Plant and growth habit*.—Relatively compact, semi-upright and mounding plant habit becoming more trailing with subsequent development; relatively moderately vigorous growth habit and moderate growth rate.

*Branching habit*.—Freely branching habit with eleven primary lateral branches each with about ten secondary lateral branches.

*Plant height, soil level to top of foliar plane*.—About 18.5 cm.

*Plant height, soil level to top of floral plane*.—About 19 cm.

*Plant diameter or spread*.—About 43 cm.

*Lateral branches*.—Length: About 22 cm. Diameter: About 4 mm. Internode length: About 1.5 cm. Strength: Strong, flexible. Texture and luster: Pubescent; semi-glossy. Color, developing: Close to 195A and 197A. Color, developed: Close to 197A.

Leaf description:

*Arrangement*.—Opposite, simple.

*Length*.—About 3.5 cm.

*Width*.—About 1.6 cm.

*Shape*.—Broadly lanceolate to ovate.

*Apex*.—Obtuse.

*Base*.—Obtuse.

*Margin*.—Entire.

*Texture and luster, upper surface*.—Pubescent; matte.

*Texture and luster, lower surface*.—Smooth, glabrous; matte.

*Venation pattern*.—Pinnate, reticulate.

*Color*.—Developing leaves, upper surface: Close to N137C. Developing leaves, lower surface: Close to 191A. Fully expanded leaves, upper surface: Close to 137A; venation, close to 147D. Fully expanded leaves, lower surface: Close to 138B; venation, close to 147D.

*Petioles*.—Length: About 6 mm. Diameter: About 3.3 mm. Strength: Moderately strong. Texture and luster, upper and lower surfaces: Smooth, glabrous; semi-glossy. Color, upper and lower surfaces: Close to 147D.

Inflorescence description:

*Form and aspect*.—Single (daisy) inflorescence form with ray and disc florets developing acropetally on a pyramidal receptacle; inflorescences positioned above and beyond the foliar plane on strong peduncles; inflorescences face mostly upright to outwardly.

*Flowering habit*.—Freely flowering habit; about 1,034 inflorescences develop per plant during the flowering season.

*Fragrance*.—None detected.

*Natural flowering season*.—Plants flower continuously from April to October in Germany; early flowering habit, plants begin flowering about six weeks after planting rooted young plants.

*Inflorescence longevity*.—Inflorescences last about four days on the plant; inflorescences persistent.

*Inflorescence buds*.—Height: About 3 mm. Diameter: About 4 mm. Shape: Oblate. Texture and luster: Smooth, glabrous; semi-glossy. Color: Close to 138A.

*Inflorescence size*.—Diameter: About 1.6 cm. Depth (height): About 5 mm. Disc diameter: About 5.6 mm. Receptacle diameter: About 1 mm. Receptacle height: About 1 mm. Receptacle shape: Pyramidal. Receptacle color: Close to 191B.

*Ray florets*.—Number of ray florets per inflorescence: About 13 arranged in a single whorl. Length: About 8 mm. Width: About 2.2 mm. Shape: Elongated oblong. Apex: Emarginate or obtuse. Base: Cordate, oblique. Margin: Entire; slightly undulate. Texture and luster, upper and lower surfaces: Smooth, glabrous; satiny; matte. Color: When opening, upper surface: Close to 12A. When opening, lower surface: Close to 144B, 1A and 2B. Fully opened, upper surface: Close to 12A; venation, close to 12A; color does not change with subsequent development. Fully opened, lower surface: Close to 1A and 2B; venation, close to 144B; color does not change with subsequent development.

*Disc florets*.—Number of disc florets per inflorescence: About 50 massed at the center of the inflorescence. Length: About 2 mm. Diameter: About 1 mm. Shape: Tubular, elongated; apex dentate. Texture and luster, inner surface: Smooth, glabrous; matte. Texture and luster, outer surface: Smooth, glabrous; semi-glossy. Color, immature, inner surface: Close to 144A. Color, immature, outer surface: Close to 157C. Color, mature, inner surface: Close to 144A. Color, mature, outer surface: Close to 144A and 155C.

*Phyllaries*.—Quantity per inflorescence: About ten to twelve in a single whorl. Length: About 2.6 cm. Width: About 1.2 cm. Shape: Nearly round to obcordate. Apex: Acute. Base: Cordate, oblique. Margin: Entire. Texture and luster, upper and lower surfaces: Smooth, glabrous; semi-glossy. Color, upper surface: Close to N137D. Color, lower surface: Close to 191A.

*Peduncles*.—Length, terminal peduncle: About 1.8 cm. Length, third peduncle: About 3 cm. Diameter, terminal peduncle: About 2.5 mm. Diameter, third peduncle: About 1 mm. Strength: Strong; flexible. Texture and luster: Smooth, glabrous; semi-glossy. Color: Close to 195A and N199B.

*Reproductive organs*.—Androecium (present on ray and disc florets): Quantity per disc floret: Two. Filament length: About 1 mm. Filament color: Close to 12A. Anther length: About 0.5 mm. Anther shape: Oblong. Anther color: Close to 12A. Pollen amount: Scarce. Pollen color: Close to 12A. Gynoecium (present on disc florets only): Pistil length: About 2.2 mm. Style length: About 1 mm. Style color: Close to 145D. Stigma diameter: About 0.8 mm. Stigma shape: Bi-parted. Stigma color: Close to 12A. Ovary color: Close to 145D.

*Fruits and seeds*.—To date, fruit and seed development have not been observed on plants of the new *Sanvitalia*.

Pathogen & pest resistance: To date, plants of the new *Sanvitalia* have not been shown to be resistant to pathogens and pests common to *Sanvitalia* plants.

Garden performance: Plants of the new Clematis have exhibited good tolerance to rain and wind and have been observed to tolerate temperatures from about 3° C. to about 28° C. and to be suitable for USDA Hardiness Zone 11.

It is claimed:

1. A new and distinct *Sanvitalia* plant named 'Dosansusugo24' as herein illustrated and described.

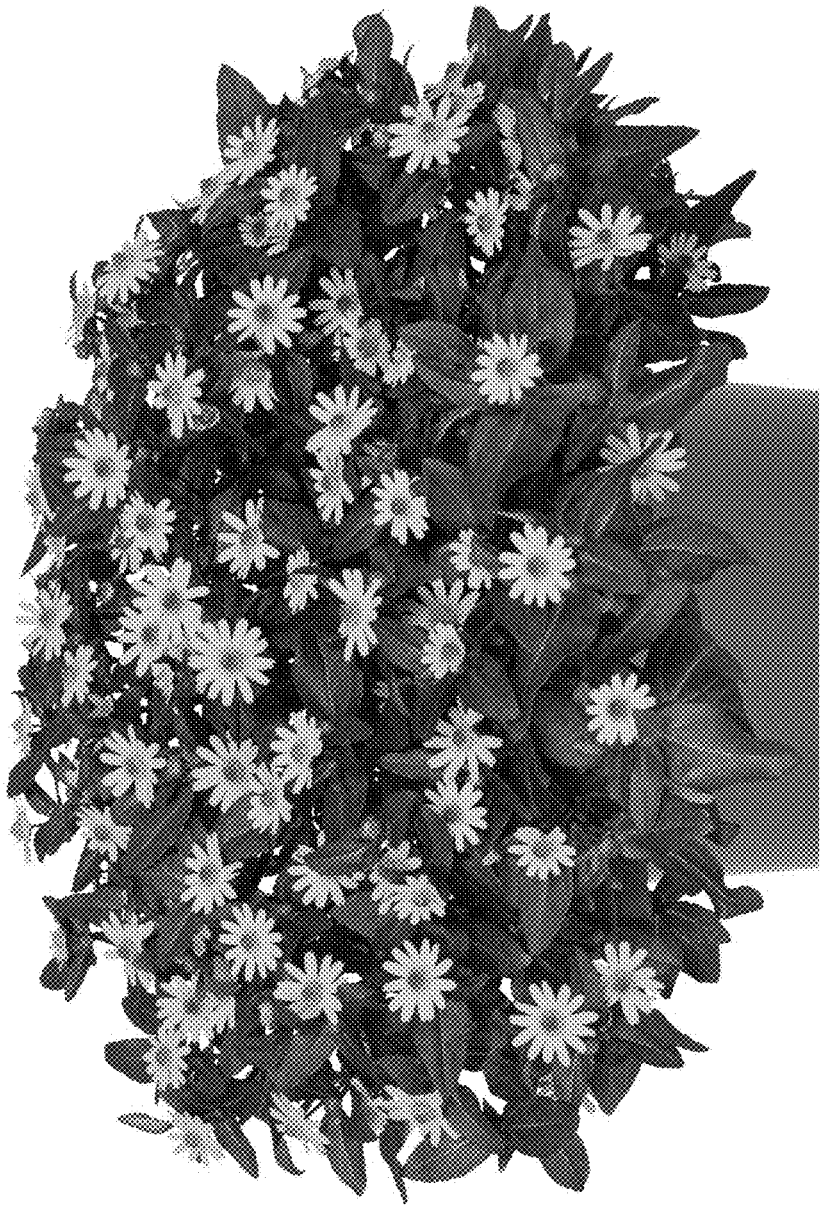

* * * * *